(12) United States Patent
Zhang

(10) Patent No.: US 11,342,913 B2
(45) Date of Patent: May 24, 2022

(54) REVERSE CURRENT SWITCH

(71) Applicant: SHENZHEN GOODIX TECHNOLOGY CO., LTD., Shenzhen (CN)

(72) Inventor: Mengwen Zhang, Shenzhen (CN)

(73) Assignee: SHENZHEN GOODIX TECHNOLOGY CO., LTD., Shenzhen (CN)

( * ) Notice: Subject to any disclaimer, the term of this patent is extended or adjusted under 35 U.S.C. 154(b) by 269 days.

(21) Appl. No.: 16/686,097

(22) Filed: Nov. 16, 2019

(65) Prior Publication Data

US 2020/0083885 A1 Mar. 12, 2020

Related U.S. Application Data

(63) Continuation of application No. PCT/CN2018/103680, filed on Aug. 31, 2018.

(51) Int. Cl.
*H03K 17/687* (2006.01)
*A61B 5/024* (2006.01)
*H03K 3/0233* (2006.01)
*H04R 1/10* (2006.01)

(52) U.S. Cl.
CPC ..... *H03K 17/6872* (2013.01); *A61B 5/02444* (2013.01); *H03K 3/02337* (2013.01); *H04R 1/1041* (2013.01)

(58) Field of Classification Search
CPC ............ H03K 17/6872; H03K 3/02337; A61B 5/02444; H04R 1/1041

USPC ........................................................ 600/508
See application file for complete search history.

(56) References Cited

U.S. PATENT DOCUMENTS

| 6,518,733 | B1 | 2/2003 | Schenkel et al. |
| 6,636,021 | B2 | 10/2003 | Schenkel et al. |
| 2003/0090240 | A1 | 5/2003 | Schenkel et al. |
| 2011/0121659 | A1 | 5/2011 | Cheng et al. |
| 2011/0199351 | A1 | 8/2011 | Kurokawa |
| 2014/0347902 | A1 | 11/2014 | Cheng et al. |
| 2017/0295632 | A1 | 10/2017 | Sun |
| 2018/0138860 | A1 | 5/2018 | Zhang |
| 2018/0192183 | A1 | 7/2018 | Mackay |

FOREIGN PATENT DOCUMENTS

| CN | 101106324 A | 1/2008 |
| CN | 102545780 A | 7/2012 |
| CN | 203313144 U | 11/2013 |
| CN | 103531634 A | 1/2014 |
| CN | 105897012 A | 8/2016 |
| CN | 107769758 A | 3/2018 |

(Continued)

*Primary Examiner* — Tomi Skibinski

(57) ABSTRACT

Provided is a reverse current switch. The reverse current switch includes: a comparison unit including a first input end, a second input end, and a first output end; and a switch resistance unit, where a first end of the switch resistance unit is connected to the first input end, a second end of the switch resistance unit is connected to the second input end, and a third end of the switch resistance unit is connected to the output end of the comparison unit, and the switch resistance unit is controlled by a voltage of the first output end. This reverse current switch has a simple structure and can implement working under low voltage conditions.

17 Claims, 5 Drawing Sheets

(56) References Cited

FOREIGN PATENT DOCUMENTS

| JP | 2001051735 | A |   | 2/2001 |
|----|------------|---|---|--------|
| JP | 2004213697 | A | * | 7/2004 |
| JP | 2004213697 | A |   | 7/2004 |

* cited by examiner

REVERSE CURRENT SWITCH

CROSS REFERENCE TO RELATED APPLICATIONS

The present disclosure is a continuation of international application No. PCT/CN2018/103680, filed on Aug. 31, 2018, which is hereby incorporated by reference in its entirety.

TECHNICAL FIELD

The present disclosure relates to the technical field of electronics, and in particular, to a reverse current switch.

BACKGROUND

In some power supply systems, in order to prevent a power-supplied circuit from being affected by abnormal operation of a power supply system, it is usually necessary to add a reverse current switch between the two. For example, in the case of power supply application of a wire-controlled earphone, as shown in FIG. 1, in order to expand the application of the wire-controlled earphone, such as adding an expansion circuit like a heart rate sensor, it is necessary to bias Vdd from an earphone port to gain additional power. The wire-controlled earphone includes a microphone and a button. Since a mobile phone supplies power to the wire-controlled earphone through a resistor R0 of which a resistance value is generally large, a current that the expansion circuit can obtain from the mobile phone is limited. In order to ensure normal operation of the expansion circuit, the expansion circuit generally includes a large capacitor for energy storage, that is, C1 in FIG. 1. In order to prevent a charge on the C1 from being discharged when Vdda is brought down, for example, the earphone port of the mobile phone is hibernated or the button is pressed, it is necessary to add a reverse current switch between Vdda and Vddb. An existing reverse current switch is relatively complicated in structure.

SUMMARY

In view of this, an embodiment of the present disclosure provides a reverse current switch, which has a simple structure and can implement working under low voltage conditions.

In a first aspect, provided is a reverse current switch. The reverse current switch includes: a comparison unit including a first input end, a second input end, and a first output end; and a switch resistance unit, where a first end of the switch resistance unit is connected to the first input end, a second end of the switch resistance unit is connected to the second input end, and a third end of the switch resistance unit is connected to the output end of the comparison unit, and the switch resistance unit is controlled by a voltage of the first output end, where when a voltage of the first input end is greater than a voltage of the second input end, the voltage of the first output end controls the switch resistance unit to be in an on state; or when a voltage of the first input end is less than a voltage of the second input end, the voltage of the first output end controls the switch resistance unit to be in an off state.

The comparison unit controls the on or off of the switch resistance unit, thereby implementing a simple structure, low power consumption, and working under low voltage conditions.

In one possible implementation manner, the reverse current switch further includes: a voltage controlled unit including a voltage controlled resistance unit and a voltage controlled voltage generation unit, where the voltage controlled resistance unit and the switch resistance unit are connected in series between the first input end and the second input end, the voltage controlled voltage generation unit is connected in parallel with the comparison unit, and the voltage controlled voltage generation unit includes a second output end, where when a difference between the voltage of the first input end and the voltage of the second input end increases, a voltage output by the voltage controlled voltage generation unit controls a resistance value of the voltage controlled resistance unit to decrease; or when a difference between the voltage of the first input end and the voltage of the second input end decreases, a voltage output by the voltage controlled voltage generation unit controls a resistance value of the voltage controlled resistance unit to increase.

Current detection accuracy of the reverse current switch can be improved by adding the voltage controlled unit.

In one possible implementation manner, the comparison unit includes: a first metal—oxide—semiconductor (MOS) transistor, a second MOS transistor, a third MOS transistor, and a fourth MOS transistor, where a gate of the first MOS transistor is connected to a gate of the second MOS transistor, a gate of the third MOS transistor is connected to a gate of the fourth MOS transistor and a source of the third MOS transistor is connected to a source of the fourth MOS transistor, a drain of the first MOS transistor is connected to a drain of the third MOS transistor, a drain of the second MOS transistor and a drain of the fourth MOS transistor are respectively connected to the first output end, a source of the first MOS transistor is connected to the first input end, and a source of the second MOS transistor is connected to the second input end.

In one possible implementation manner, the first MOS transistor and the second MOS transistor are PMOS transistors, the third MOS transistor and the fourth MOS transistor are NMOS transistors, the gate of the third MOS transistor and the gate of the fourth MOS transistor are respectively connected to a bias unit, and the source of the first MOS transistor is connected to the drain of the first MOS transistor.

In one possible implementation manner, the first MOS transistor and the second MOS transistor are PMOS transistors, the third MOS transistor and the fourth MOS transistor are NMOS transistors, the gate of the first MOS transistor and the gate of the second MOS transistor are respectively connected to a bias unit, and the source of the third MOS transistor is connected to the drain of the third MOS transistor.

In one possible implementation manner, the reverse current switch further includes: a voltage controlled unit including a voltage controlled resistance unit and a voltage controlled voltage generation unit, where the voltage controlled resistance unit and the switch resistance unit are connected in series between the first input end and the source of the second MOS transistor; the voltage controlled voltage generation unit includes a second output end, and includes a fifth MOS transistor that is a PMOS transistor and a first resistor, a drain of the fifth MOS transistor and one end of the first resistor are respectively connected to the second output end, a source of the fifth MOS transistor is connected to the second input end, a gate of the fifth MOS transistor is connected to the gate of the first MOS transistor, and the other end of the first resistor is connected to the source of the third MOS transistor; and the voltage controlled resistance unit is controlled by a voltage of the second output end.

In one possible implementation manner, the reverse current switch further includes: a voltage controlled unit including a voltage controlled resistance unit and a voltage controlled voltage generation unit, where the voltage controlled resistance unit and the switch resistance unit are connected in series between the first input end and the source of the second MOS transistor; the voltage controlled voltage generation unit includes a second output end, and includes a fifth MOS transistor that is an NMOS transistor and a first resistor, a drain of the fifth MOS transistor and one end of the first resistor are respectively connected to the second output end, the other end of the first resistor is connected to the second input end, a gate of the fifth MOS transistor is connected to the gate of the third MOS transistor, and a source of the fifth MOS transistor is connected to the source of the third MOS transistor; and the voltage controlled resistance unit is controlled by a voltage of the second output end.

In one possible implementation manner, the reverse current switch further includes: a hysteresis generation unit, where when the voltage of the first input end is greater than the voltage of the second input end, the hysteresis generation unit increases a current of the fourth MOS transistor and/or decreases a current of the second MOS transistor; or when the voltage of the first input end is less than the voltage of the second input end, the hysteresis generation unit decreases a current of the fourth MOS transistor and/or increases a current of the second MOS transistor.

By adjusting the current of the MOS transistor in the comparison unit, it is advantageous to provide a certain hysteresis range so that the reverse current switch is not frequently flipped by disturbance of a critical point.

In one possible implementation manner, the reverse current switch further includes: an offset correction unit, where when the voltage of the first input end is equal to the voltage of the second input end, the offset correction unit performs offset correction on the reverse current switch.

Optionally, the offset correction unit may be a reset switch connected in parallel with the switch resistance unit or in parallel with the switch resistance unit and the voltage controlled resistance unit. When the reset switch is turned on, the voltage of the first input end is equal to the voltage of the second input end. A width to length ratio of the third MOS transistor to the fourth MOS transistor may be fine-tuned such that a current ratio of the fourth MOS transistor to the third MOS transistor is equal to a current ratio of the second MOS transistor to the first MOS transistor as much as possible.

By performing offset correction on the reverse current switch, a current detection dead zone of the reverse current switch can be greatly reduced.

In one possible implementation manner, the switch resistance unit is composed of a sixth MOS transistor and a second resistor in series, and a gate of the sixth MOS transistor is controlled by the voltage of the output end of the comparison unit.

In one possible implementation manner, the voltage controlled resistance unit is composed of a seventh MOS transistor and a third resistor in parallel, and a gate of the seventh MOS transistor is controlled by the voltage of the output end of the voltage controlled voltage generation unit.

In one possible implementation manner, the first input end is connected to a power supply circuit, and the second input end is connected to a load circuit, where when the voltage of the first input end is greater than the voltage of the second input end, the power supply circuit charges a storage capacitor between the load circuit and the power supply circuit; or when the voltage of the first input end is less than the voltage of the second input end, a storage capacitor is discharged to the load circuit.

In one possible implementation manner, the power supply circuit is a wire-controlled earphone, and the load circuit is a heart rate sensor.

These and other aspects of the present disclosure will be clearer and easier to understand from the following description of the embodiments.

DESCRIPTION OF EMBODIMENTS

In order to make those skilled in the art better understand technical solutions in embodiments of the present disclosure, a clear and complete description of the technical solutions in the embodiments of the present disclosure will be given below, in combination with the accompanying drawings in the embodiments of the present disclosure. Apparently, the embodiments described are merely a part, but not all, of the embodiments of the present disclosure. All of other embodiments, obtained by those skilled in the art based on the embodiments of the present disclosure, shall fall into the protection scope of the embodiments of the present disclosure.

Figure 1:
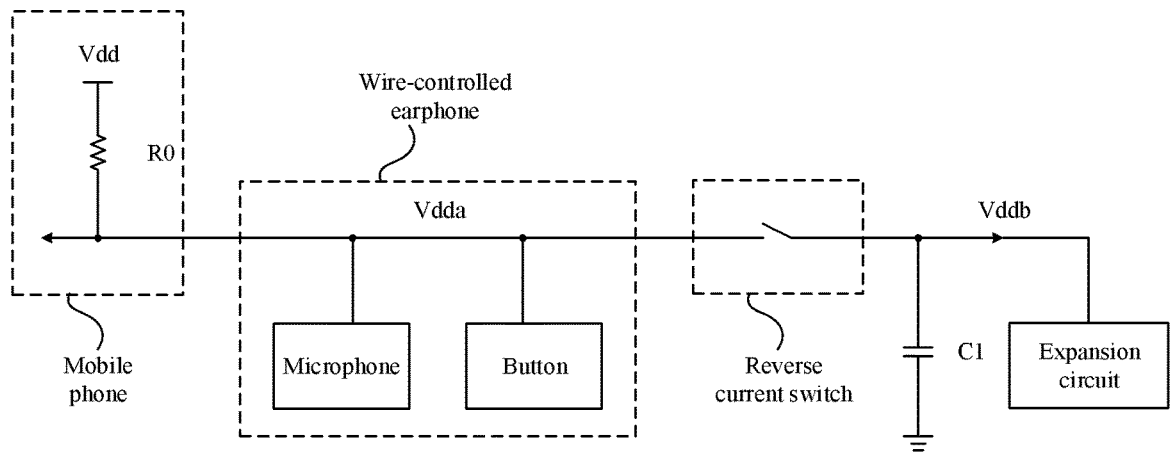
FIG. 1 is a schematic diagram of a power supply system provided by an embodiment of the present disclosure.

FIG. 1 shows a schematic diagram of a power supply system provided by an embodiment of the present disclosure. The power supply system includes a power supply circuit, a load circuit, a reverse current switch, and a storage capacitor. The power supply circuit may be a wire-controlled earphone of FIG. 1, and the load circuit may be an expansion circuit of FIG. 1. When a voltage supplied by the power supply circuit is greater than a voltage input to the load circuit, the reverse current switch may be turned on, so that the power supply circuit charges the storage capacitor. When a voltage supplied by the power supply circuit is less than a voltage input to the load circuit, the reverse current switch is turned off, and the storage capacitor is discharged to the load circuit. It should be noted that the reverse current switch provided by the embodiment of the present disclosure is not limited to the application scenario of FIG. 1, and the reverse current switch provided by the embodiment of the present disclosure may be used as long as a switch for preventing reverse current is required in a power supply system, for example, a weak power supply system.

Figure 2:
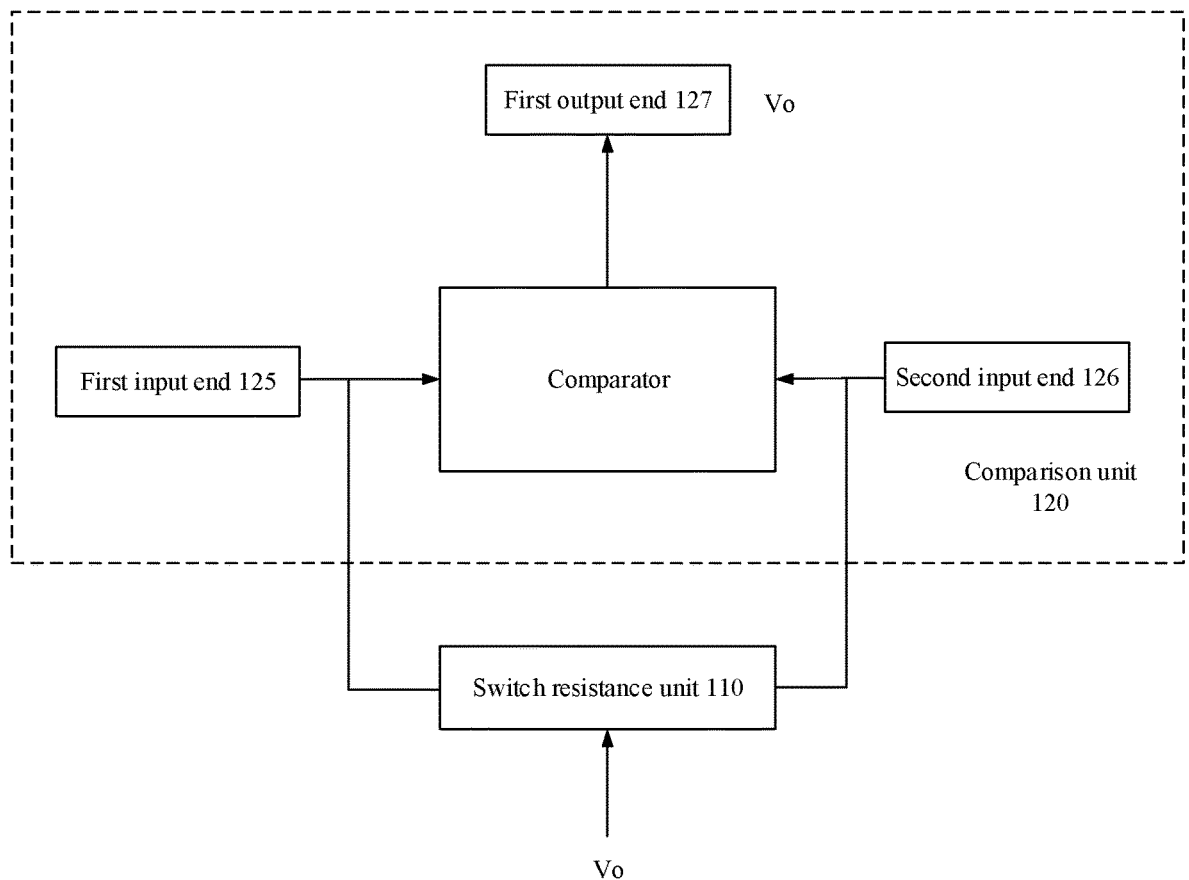
FIG. 2 is a schematic block diagram of a reverse current switch provided by the present disclosure.

The reverse current switch in the embodiment of the present disclosure may be mainly composed of two parts: a switch resistance unit and a comparison unit. Specifically, as shown in FIG. 2, the reverse current switch includes a switch resistance unit 110 and a comparison unit 120 including a first input end 125, a second input end 126, and a first output end 127. A first end of the switch resistance unit 110 is connected to the first input end 125, a second end of the switch resistance unit 110 is connected to the second input end 126, and a third end of the switch resistance unit 110 is connected to the first output end 127, and the switch resistance unit 110 is controlled by a voltage of the first output end 127. A voltage of the first input end 125 and a voltage of the second input end 126 of the comparison unit may be Vdda and Vddb of FIG. 1, respectively, that is, a voltage provided by the power supply circuit and an input voltage of the load circuit.

When Vdda is greater than Vddb, the voltage of the output end of the comparison unit may control the switch resistance unit to be in an on state, and then the power supply circuit may charge the C1 in FIG. 1. When Vdda is less than Vddb, the voltage of the output end of the comparison unit may control the switch resistance unit to be in an off state, and then the C1 may be discharged to the load circuit.

The reverse current switch of the present disclosure will be described in detail below with reference to specific embodiments.

Figure 3:
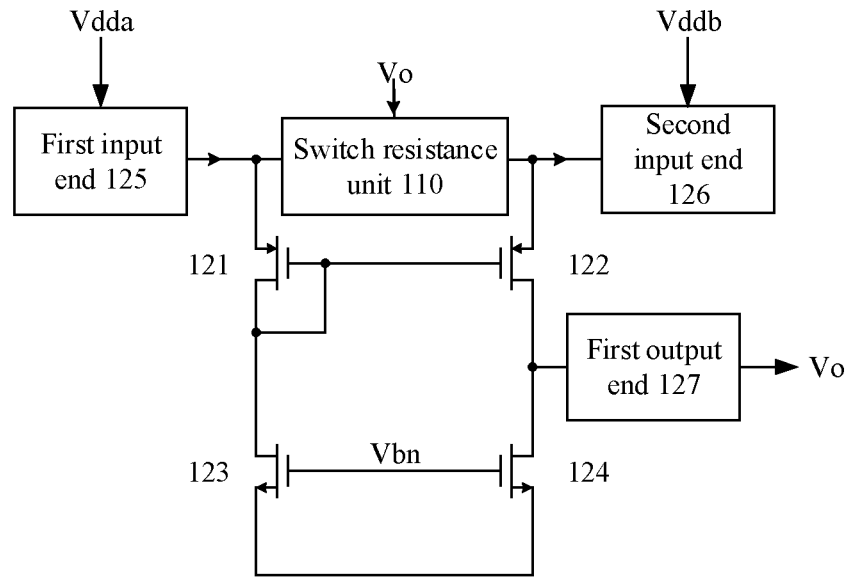
FIG. 3 is a schematic circuit diagram of a reverse current switch according to an embodiment of the present disclosure.

FIG. 3 is a schematic circuit diagram of a reverse current switch according to an embodiment of the present disclosure. As shown in FIG. 3, the reverse current switch may include a switch resistance unit 110 and a comparison unit composed of a first MOS transistor 121, a second MOS transistor 122, a third MOS transistor 123, a fourth MOS transistor 124, a first input end 125, a second input end 126, and a first output end 127. A first end of the switch resistance unit 110 is connected to the first input end 125, and a second end of the switch resistance unit 110 is connected to the second input end 126, a gate of the first MOS transistor 121 is connected to a gate of the second MOS transistor 122, the gate of the first MOS transistor 121 is connected to a drain of the first MOS transistor 121, and a gate of the third MOS transistor 123 and a gate of the fourth MOS transistor 124 are respectively connected to a bias unit other than the reverse current switch, and a bias voltage provided by the bias unit is Vbn as shown in FIG. 3. The drain of the first MOS transistor 121 is connected to a drain of the third MOS transistor 123, a drain of the second MOS transistor 122 is connected to a drain of the fourth MOS transistor 124, a source of the third MOS transistor 123 is connected to a source of the fourth MOS transistor 124, a source of the first MOS transistor 121 is connected to the first input end 125, a source of the second MOS transistor 122 is connected to the second input end 126, a voltage of the first input end 125 is Vdda in FIG. 3, and a voltage of the second input end 126 is Vddb in FIG. 3, that is, the first input end 125 is connected to a power supply circuit, and the second input end 126 is connected to a load circuit. The drain of the second MOS transistor 122 and the drain of the fourth MOS transistor 124 are respectively connected to the first output end 127, or in other words, the drain of the second MOS transistor 122 and the drain of the fourth MOS transistor 124 are connected to each other and serve as the first output end 127. An output voltage of the first output end is Vo, a third end of the switch resistance unit 110 is connected to the first output end 127, and the switch resistance unit 110 is controlled by the output voltage Vo of the first output end 127.

It should be noted that a direction of arrow in the circuit diagram is a direction of current, and is not used to limit the type of the MOS transistor. In FIG. 3, the first MOS transistor 121 and the second MOS transistor 122 are PMOS transistors respectively, and the third MOS transistor 123 and the fourth MOS transistor 124 are NMOS transistors respectively.

Figure 4:
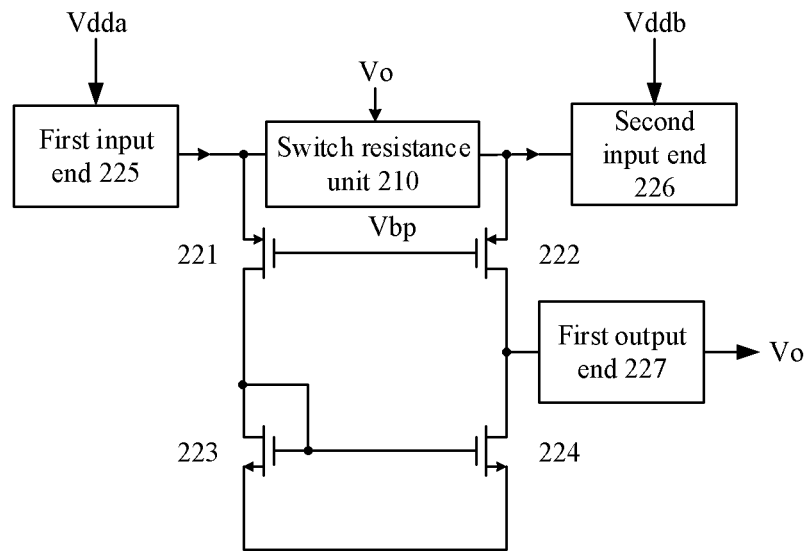
FIG. 4 is a schematic circuit diagram of a reverse current switch according to another embodiment of the present disclosure.

FIG. 4 is a schematic circuit diagram of a reverse current switch according to another embodiment of the present disclosure. As shown in FIG. 4, the reverse current switch may include a switch resistance unit 210 and a comparison unit including a first MOS transistor 221, a second MOS transistor 222, a third MOS transistor 223, a fourth MOS transistor 224, a first input end 225, a second input end 226, and a first output end 227. A first end of the switch resistance unit 210 is connected to the first input end 225, and a second end of the switch resistance unit 210 is connected to the second input end 226, a gate of the first MOS transistor 221 and a gate of the second MOS transistor 222 are respectively connected to a bias unit other than the reverse current switch, and a bias voltage provided by the bias unit is Vbp as shown in FIG. 4. A gate of the third MOS transistor 223 is connected to a gate of the fourth MOS transistor 224, the gate of the third MOS transistor 223 is connected to a drain of the third MOS transistor 223, a drain of the first MOS transistor 221 is connected to the drain of the third MOS transistor 223, a drain of the second MOS transistor 222 is connected to a drain of the fourth MOS transistor 224, a source of the third MOS transistor 223 is connected to a source of the fourth MOS transistor 224, a source of the first MOS transistor 221 is connected to the first input end 225, and a source of the second MOS transistor 222 is connected to the second input end 226, a voltage of the first input end 225 is Vdda in FIG. 4, and a voltage of the second input end 226 is Vddb in FIG. 4, that is, the first input end 225 is connected to a power supply circuit, and the second input end 226 is connected to a load circuit. The drain of the second MOS transistor 222 and the drain of the fourth MOS transistor 224 are connected to the first output end 227, or in other words, the drain of the second MOS transistor 222 and the drain of the fourth MOS transistor 224 are connected to each other and serve as the first output end 227. An output voltage of the first output end is Vo, a third end of the switch resistance unit 210 is connected to the first output end 227, and the switch resistance unit 210 is controlled by the output voltage Vo of the first output end 227.

It should be noted that a direction of arrow in the circuit diagram is a direction of current, and is not used to limit the type of the MOS transistor. In FIG. 4, the first MOS transistor 221 and the second MOS transistor 222 are PMOS transistors respectively, and the third MOS transistor 223 and the fourth MOS transistor 224 are NMOS transistors respectively.

A working principle of the reverse current switch in the embodiment of the present disclosure will be described below with reference to FIG. 3 or FIG. 4.

Optionally, when the reverse current switch in the embodiment of the present disclosure is designed, a MOS transistor should be selected according to the following rules where possible: when the voltage of the first input end 125/225 is equal to the voltage of the second input end 126/226, that is, Vdda=Vddb, a current ratio of the second MOS transistor 122/222 to the first MOS transistor 121/221 may be equal to a current ratio of the fourth MOS transistor 124/224 to the third MOS transistor 123/223.

For convenience of description, in the following embodiments, it may be assumed that when a current of the fourth MOS transistor is greater than a current of the second MOS transistor, the voltage Vo of the first output end is at a low level; and when a current of the fourth MOS transistor is less than a current of the second MOS transistor, the voltage Vo of the first output end is at a high level.

For example, when Vdda=Vddb, a current ratio of the second MOS transistor 122/222 to the first MOS transistor 121/221 and a current ratio of the fourth MOS transistor 124/224 to the third MOS transistor 123/223 are both 1. Since the first MOS transistor 121/221 and the third MOS transistor 123/223 are connected in series, currents of the first MOS transistor 121/221 and the third MOS transistor 123/223 are equal. If the currents of the first MOS transistor 121/221 and the third MOS transistor 123/223 are set to I1, and a current of the second MOS transistor 122/222 is set to I2, I1 is equal to I2 (I1=I2), because Vdda is equal to Vddb (Vdda=Vddb). Since the current ratio is 1, a current of the fourth MOS transistor 124/224 is also I1. In a case where Vdda increases and Vddb remains unchanged, I1 increases, and a current of the fourth MOS transistor 124/224 also increases. At this time, the increase of Vdda causes gate voltages of the first MOS transistor 121/221 and the second MOS transistor 122/222 to increase, so that a current I2 of the second MOS transistor 122/222 decreases (Vddb remains unchanged), and thus I1 is greater than I2, a voltage Vo of the first output end is at a low level, and the switch resistance unit 110/210 is controlled to be in an on state. Similarly, in a case where Vdda decreases and Vddb remains unchanged, I1 decreases, and a current of the fourth MOS transistor 124/224 also decreases. At this time, the decrease of Vdda causes gate voltages of the first MOS transistor 121/221 and the second MOS transistor 122/222 to decrease, so that a current I2 of the second MOS transistor 122/222 increases (Vddb remains unchanged), and thus I1 is less than I2, a voltage Vo of the first output end is at a high level, and the switch resistance unit 110/210 is controlled to be in an off state.

For another example, when Vdda=Vddb, a current ratio of the second MOS transistor 122/222 to the first MOS transistor 121/221 and a current ratio of the fourth MOS transistor 124/224 to the third MOS transistor 123/223 are both 2. Assuming that currents of the first MOS transistor 121/221 and the third MOS transistor 123/223 are 1 mA, since the current ratio is 2, currents of the second MOS transistor 122/222 and the fourth MOS transistor 124/224 are both 2 mA. In a case where Vdda increases and Vddb remains unchanged, currents of the first MOS transistor 121/221 and the third MOS transistor 123/223 increase, and a current of the fourth MOS transistor 124/224 also increases, that is, being greater than 2 mA. At this time, the increase of Vdda causes gate voltages of the first MOS transistor 121/221 and the second MOS transistor 122/222 to increase, so that a current of the second MOS transistor 122/222 decreases (Vddb remains unchanged), that is, being less than 2 mA, and thus the current of the fourth MOS transistor 124/224 is greater than the current of the second MOS transistor, a voltage Vo of the first output end is at a low level, and the switch resistance unit 110/210 is controlled to be in an on state. Similarly, in a case where Vdda decreases and Vddb remains unchanged, currents of the first MOS transistor 121/221 and the third MOS transistor 123/223 decrease, and a current of the fourth MOS transistor 124/224 also decreases, that is, being less than 2 mA. At this time, the decrease of Vdda causes gate voltages of the first MOS transistor 121/221 and the second MOS transistor 122/222 to decrease, so that a current of the second MOS transistor 122/222 increases (Vddb remains unchanged), that is, being greater than 2 mA, and thus the current of the fourth MOS transistor 124/224 is less than the current of the second MOS transistor, a voltage Vo of the first output end is at a high level, and the switch resistance unit 110/210 is controlled to be in an off state.

It should be understood that the above is an analysis of the working principle of the reverse current switch by taking cases where Vddb remains unchanged, and Vdda increases or decreases as an example. Similarly, for cases where Vdda remains unchanged, and Vddb increases or decreases, the working principle of the reverse current switch provided by the embodiment of the present disclosure is also applicable. For brevity, no further details are provided herein.

For the reverse current switch in the embodiment of the present disclosure, in an on case, the smaller a resistance value of the switch resistance unit is, the smaller a voltage drop across the switch resistance unit is, and the higher a voltage provided for a load circuit is. That is, the smaller the resistance value of the switch resistance unit is, the better it is. In terms of sensitivity requirements, the larger a resistance value of the switch resistance unit is, the better it is; and current detection accuracy of the reverse current switch could be improved. Therefore, the reverse current switch in the embodiment of the present disclosure further includes:

a voltage controlled unit including a voltage controlled resistance unit and a voltage controlled voltage generation unit, where the voltage controlled resistance unit and the switch resistance unit are connected in series between the first input end and the second input end, and the voltage controlled voltage generation unit is connected in parallel with the comparison unit, and the voltage controlled voltage generation unit includes a second output end, where when a difference between the voltage of the first input end and the voltage of the second input end increases, a voltage of the second output end controls a resistance value of the voltage controlled resistance unit to decrease; or when a difference between the voltage of the first input end and the voltage of the second input end decreases, a voltage of the second output end controls a resistance value of the voltage controlled resistance unit to increase.

Figure 5:
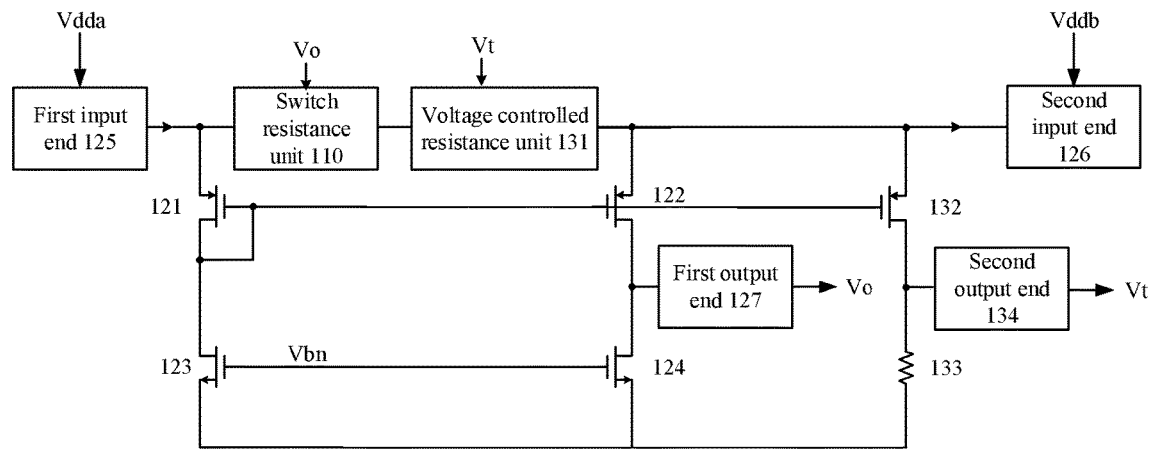
FIG. 5 is a schematic circuit diagram of a reverse current switch according to yet another embodiment of the present disclosure.

FIG. 5 is a schematic circuit diagram of a reverse current switch according to yet another embodiment of the present disclosure. FIG. 5 is a diagram showing addition of a voltage controlled unit based on FIG. 3. Specifically, the voltage controlled unit includes a voltage controlled resistance unit 131 and a voltage controlled voltage generation unit composed of a fifth MOS transistor 132 and a first resistor 133. The voltage controlled resistance unit 131 and the switch resistance unit 110 are connected in series between the first input end 125 and the source of the second MOS transistor 122, a drain of the fifth MOS transistor 132 and one end of the first resistor 133 are respectively connected to a second output end 134, and a voltage of the second output end is Vt in FIG. 5. A source of the fifth MOS transistor 132 is connected to the second input end 126, a gate of the fifth MOS transistor 132 is connected to the gate of the first MOS transistor 121, the other end of the first resistor 133 is connected to the source of the third MOS transistor 123, the fifth MOS transistor 132 is a PMOS transistor, and the voltage controlled resistance unit 131 is controlled by the voltage Vt of the second output end 134.

Figure 6:
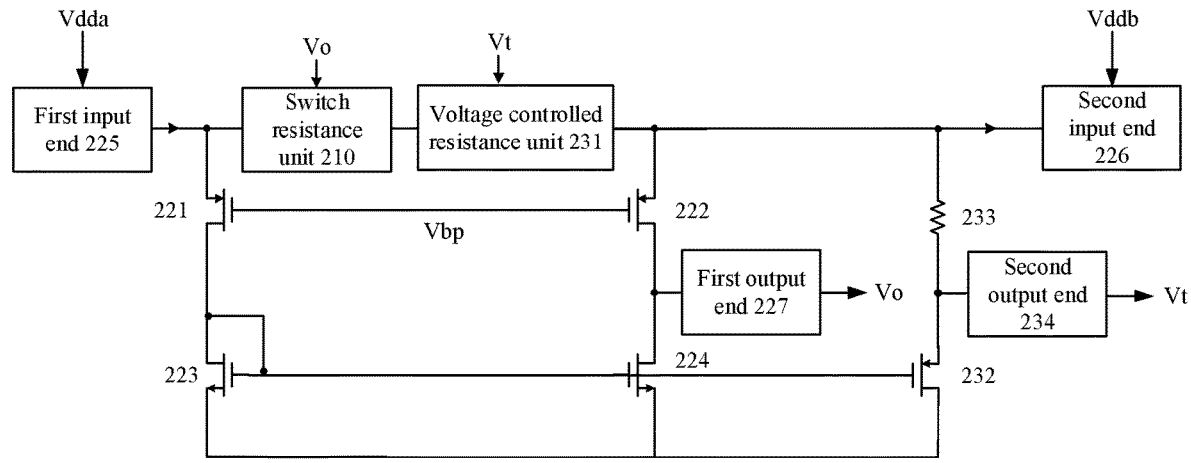
FIG. 6 is a schematic circuit diagram of a reverse current switch according to yet another embodiment of the present disclosure.

FIG. 6 is a schematic circuit diagram of a reverse current switch according to yet another embodiment of the present disclosure. FIG. 6 is a diagram showing addition of a voltage controlled unit based on FIG. 4. Specifically, the voltage controlled unit includes a voltage controlled resistance unit 231 and a voltage controlled voltage generation unit composed of a fifth MOS transistor 232 and a first resistor 233. The voltage controlled resistance unit 231 and the switch resistance unit 210 are connected in series between the first input end 225 and the source of the second MOS transistor 222, a drain of the fifth MOS transistor 232 and one end of the first resistor 233 are respectively connected to a second output end 234, and a voltage of the second output end is Vt in FIG. 6. A source of the fifth MOS transistor 232 is connected to the source of the third MOS transistor 223, a gate of the fifth MOS transistor 232 is connected to the gate of the third MOS transistor 223, the other end of the first resistor 233 is connected to the second input end 226, the fifth MOS transistor 232 is an NMOS transistor, and the voltage controlled resistance unit 231 is controlled by the voltage Vt of the second output end 234.

A working principle of the voltage controlled unit will be analyzed below with reference to FIG. 5 or FIG. 6. In a case where Vdda is greater than Vddb, Vo is at a low level and the switch resistance unit is in an on state. When Vdda increases and Vddb remains unchanged, since the gate of the fifth MOS transistor is connected to the gate of the first MOS transistor, a gate voltage of the fifth MOS transistor increases, and further, a current of the first resistor decreases, and a voltage Vt decreases, so that resistance of the voltage controlled resistance unit decreases. Since the switch resistance unit is connected in series with the voltage controlled resistance unit, the resistance value of the voltage controlled resistance unit is much less than an on resistance of the switch resistance unit when Vdda increases to a certain value. If the switch resistance unit is selected to have a relatively small resistance value, it can meet the requirement that the voltage of the second input end is high when the switch resistance unit is turned on. In a case where the switch resistance unit is in an on state, and Vdda decreases and Vddb remains unchanged, since the gate of the fifth MOS transistor is connected to the gate of the first MOS transistor, a gate voltage of the fifth MOS transistor decreases, and further, a current of the first resistor increases, and a voltage Vt increases, so that a resistance value of the voltage controlled resistance unit gradually increases. Therefore, gradual increase of the resistance value of the voltage controlled resistance unit before Vdda is less than Vddb enables detection accuracy of the reverse current switch to be improved. Therefore, variation of a voltage difference of a reverse current switch added with a voltage controlled unit with a current of the reverse current switch is no longer linear variation.

Figure 7:
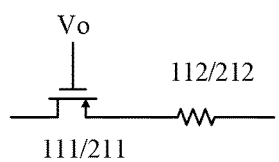
FIG. 7 is a schematic circuit diagram of a switch resistance unit in a reverse current switch provided by the present disclosure.

Optionally, in the embodiment of the present disclosure, the switch resistance unit 110/210 may be composed of a sixth MOS transistor 111/211 and a second resistor 112/212 in series in FIG. 7, and a gate voltage of the sixth MOS transistor may be provided by the output voltage Vo of the first output end. When applied to any of the embodiments of FIGS. 3 to 6, a drain of the sixth MOS transistor is connected to the first input end, and a source thereof is connected to the second input end (in the embodiments of FIGS. 3 and 4) or the voltage controlled resistance unit (in the embodiments of FIGS. 5 and 6).

Figure 8:
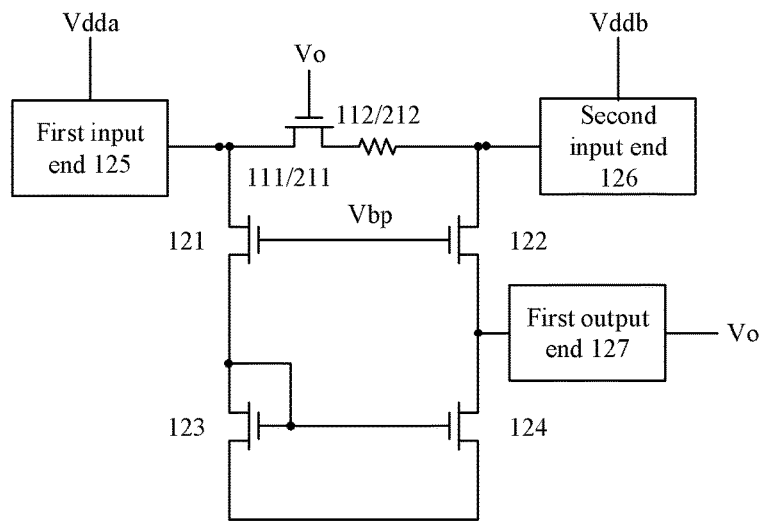
FIG. 8 is a schematic circuit diagram of a reverse current switch combining FIG. 3 and FIG. 7 provided by the present disclosure.

By way of example, FIG. 8 shows a schematic diagram of a circuit in which the switch resistance unit of FIG. 7 is applied to FIG. 3. As shown in FIG. 8, the drain of the sixth MOS transistor 111 is connected to the first input end 125, the source of the sixth MOS transistor 111 is connected to one end of the second resistor 112, the other end of the second resistor 112 is connected to the second input end 126, and a gate of the sixth MOS transistor 111 is controlled by the output voltage Vo of the first output end 127. For the remaining connection relationships, reference can be made to FIG. 3.

Figure 9:
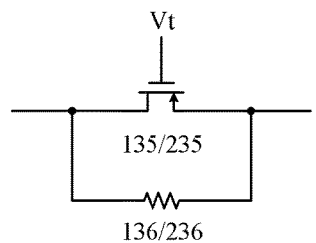
FIG. 9 is a schematic circuit diagram of a voltage controlled resistance unit in a reverse current switch provided by the present disclosure.

Optionally, in the embodiment of the present disclosure, the voltage controlled resistance unit 131/231 may be composed of a seventh MOS transistor 135/235 and a third resistor 136/236 in parallel in FIG. 9. A gate voltage of the seventh MOS transistor may be controlled by the voltage Vt of the second output end.

Figure 10:
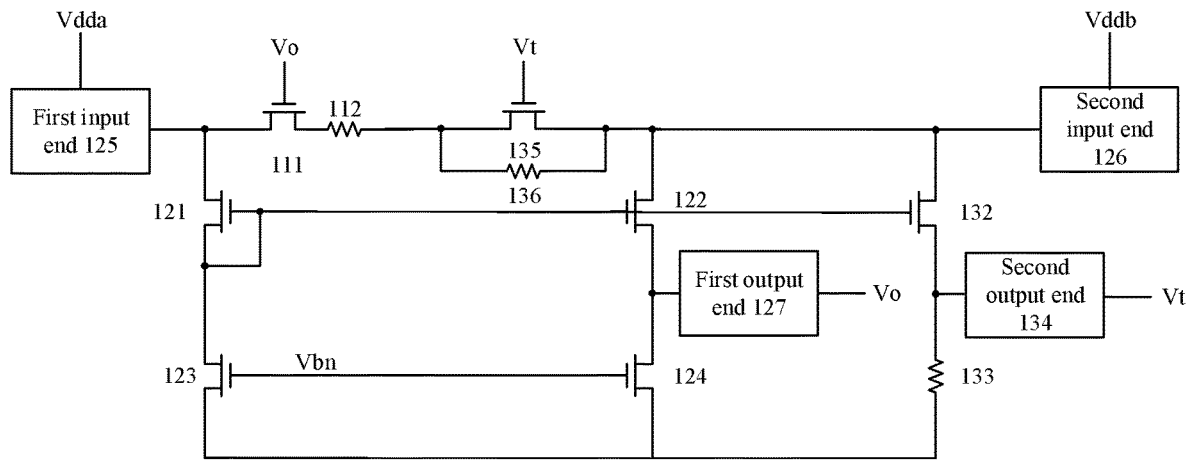
FIG. 10 is a schematic circuit diagram of a reverse current switch combining FIG. 7, FIG. 9, and FIG. 5 provided by the present disclosure.

By way of example, FIG. 10 shows a schematic diagram of a circuit in which the switch resistance unit of FIG. 7 and the voltage controlled resistance unit of FIG. 9 are applied to FIG. 5. As shown in FIG. 10, the drain of the sixth MOS transistor 111 is connected to the first input end 125, the source of the sixth MOS transistor 111 is connected to one end of the second resistor 112, the other end of the second resistor 112 is connected to one end at which the seventh MOS transistor 135 is connected in parallel with the third resistor 136, and the other end at which the seventh MOS transistor 135 is connected in parallel with the third resistor 136 is connected to the second input end 126. A gate of the sixth MOS transistor 111 is controlled by the output voltage Vo of the first output end 127, and a gate of the seventh MOS transistor 135 is controlled by the output voltage Vt of the second output end 134. For the remaining connection relationships, reference can be made to FIG. 5.

A working principle of the reverse current switch provided by the embodiment of the present disclosure will be further analyzed with reference to FIG. 10.

When Vdda is greater than Vddb, the Vo output is at a low level, and the sixth MOS transistor is in an on state, and a resistance value of the voltage controlled resistance unit controlled by Vt is a resistance value of the seventh MOS transistor and the third resistor in parallel. When Vdda continues to increase, the Vt decreases, so that the resistance value of the seventh MOS transistor and the third resistor in parallel decreases. At a certain time, the resistance value of the seventh MOS transistor and the third resistor in parallel decreases to a resistance value that is much less than a resistance value of the switch resistance unit, and the sum of the resistance values of the switch resistance unit and the voltage controlled resistance unit is a resistance value of the second resistor (the resistance value of the switch resistance unit in an on state is the resistance value of the second resistor). When Vdda decreases, the Vt increases, so that the resistance value of the seventh MOS transistor and the third resistor in parallel increases. The resistance value of the seventh MOS transistor and the third resistor in parallel is much greater than the resistance value of the switch resistance unit before Vdda is reversed from being greater than Vddb to being less than Vddb. Then the sum of the resistance values of the switch resistance unit and the voltage controlled resistance unit is the resistance value of the voltage controlled resistance unit.

It should be noted that in a case where Vdda increases and Vddb decreases, Vt decreases as well, then at this time, the resistance value of the voltage controlled resistance unit decreases gradually; in a case where Vdda decreases and Vddb increases, Vt increases as well, then at this time, the resistance value of the voltage controlled resistance unit gradually increases. In other words, when a voltage difference between the first input end and the second input end increases, the resistance value of the voltage controlled resistance unit gradually decreases; or when a voltage difference between the first input end and the second input end decreases, the resistance value of the voltage controlled resistance unit gradually increases.

Optionally, the reverse current switch in the embodiment of the present disclosure may also not need to add the voltage controlled resistance unit, and may select an adjustable resistor as a switch resistance unit.

It should be noted that, in the embodiment of the present disclosure, when the voltages of the first input end and the second input end are equal, the voltage of the first output end may control the switch resistance unit to be in an on state, and may also control the switch resistance unit to be in an off state. In other words, when the voltages of the first input end and the second input end are equal, the voltage of the first output end may be at a low level or at a high level.

Figure 11:
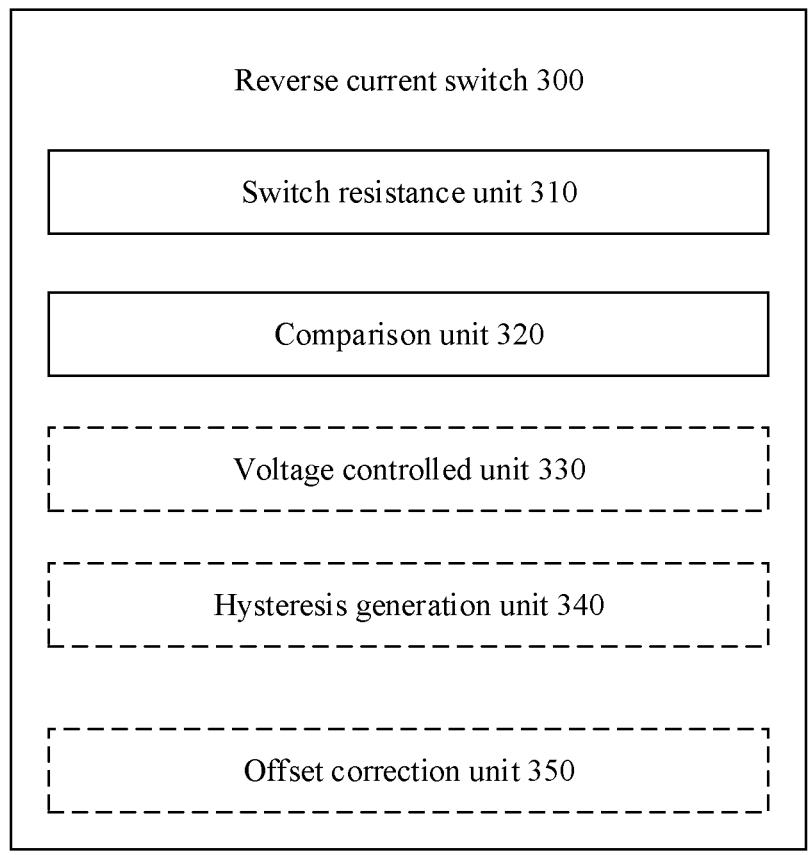
FIG. 11 is a functional block diagram of a reverse current switch provided by the present disclosure.

FIG. 11 shows a functional block diagram of a reverse current switch according to an embodiment of the present disclosure. Specifically, as shown in FIG. 11, a reverse current switch 300 includes a switch resistance unit 310 and a comparison unit 320. Optionally, the reverse current switch further includes: a voltage controlled unit 330 and a hysteresis generation unit 340. When the voltage of the first input end is greater than the voltage of the second input end, the hysteresis generation unit increases a current of the fourth MOS transistor or decreases a current of the second MOS transistor; or when the voltage of the first input end is less than the voltage of the second input end, the hysteresis generation unit decreases a current of the fourth MOS transistor or increases a current of the second MOS transistor.

This has an advantage that it can provide a certain hysteresis range, and the reverse current switch is not frequently flipped by disturbance of a critical point.

Figure 12:
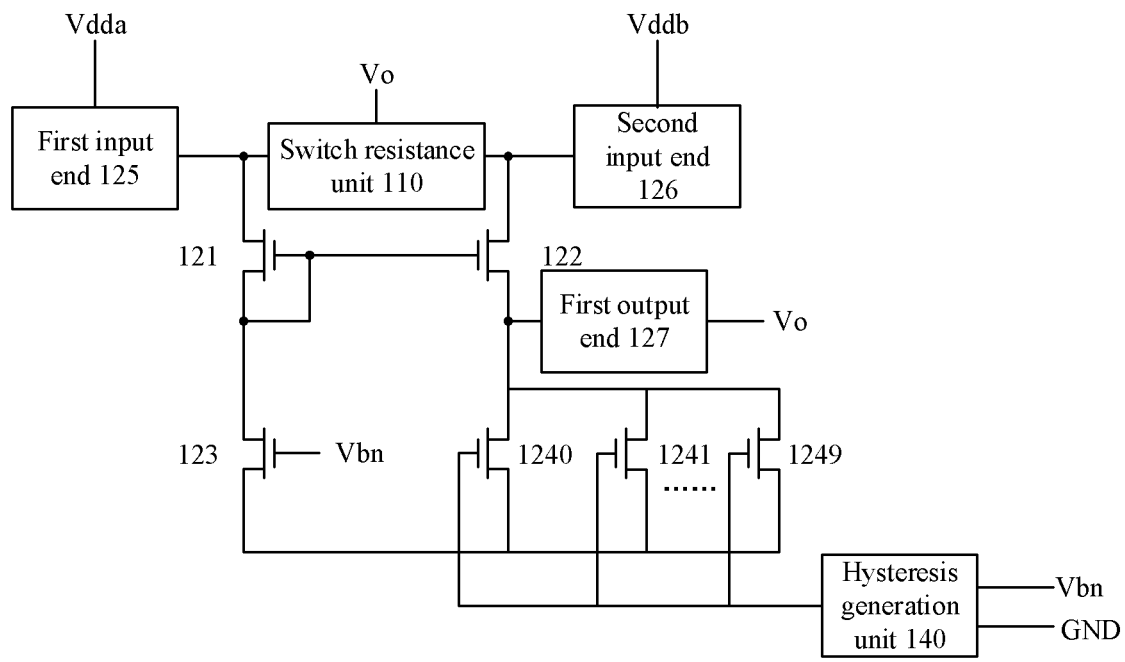
FIG. 12 is a schematic circuit diagram of a reverse current switch according to yet another embodiment of the present disclosure.

Specifically, the fourth MOS transistor may be composed of a plurality of sub-MOS transistors, and sources of the plurality of sub-MOS transistors are all connected to the source of the third MOS transistor, drains of the plurality of sub-MOS transistors are all connected to the drain of the second MOS transistor, and gates of the plurality of sub-MOS transistors are controlled by a hysteresis generation unit to be connected to a bias unit or ground. By way of an example, as shown in FIG. 12, the fourth MOS transistor 124 in FIG. 3 is composed of ten sub-MOS transistors 1240 to 1249, and a current of each of the sub-MOS transistors may be 1/10 of a current of the fourth MOS transistor 124, sources of the ten sub-MOS transistors 1240 to 1249 are all connected to the source of the third MOS transistor 123, drains of the ten sub-MOS transistors 1240 to 1249 are all connected to the drain of the second MOS transistor 122, and gates of the ten sub-MOSs transistors 1240 to 1249 are all controlled by a hysteresis generation unit to be connected to a bias unit Vbn or ground GND. For the remaining connection relationships, reference can be made to FIG. 3. Assuming that a critical point voltage Vo at which the reverse current switch is flipped is 2 V, and the reverse current switch is subjected to disturbance of 0.1 V, when Vdda is greater than Vddb at a certain time, the hysteresis generation unit controls gates of the sub-MOS transistors 1240 to 1244 of the fourth MOS transistor 124 to be connected to Vbn and gates of the sub-MOS transistors 1245 to 1249 to be connected to GND, and Vo is close to 2 V, and the hysteresis generation unit may control the gates of the three sub-MOS transistors 1245 to 1247 in the sub-MOS transistors 1245 to 1249 to be connected to the Vbn, so that Vo decreases to 1.8 V, that is, the disturbance of 0.1 V is not enough to make Vo reversed at the critical point of 2 V. Similarly, when Vdda is less than Vddb at a certain time, gates of the sub-MOS transistors 1240 to 1244 of the fourth MOS transistor 124 are connected to Vbn, and gates of the sub-MOS transistors 1245 to 1249 are connected to GND, and Vo is close to 2 V, and the hysteresis generation unit may control the gates of the three sub-MOS transistors 1240 to 1242 in the sub-MOS transistors 1240 to 1244 to be connected to the GND, so that Vo increases to 2.2 V, and similarly, the disturbance of 0.1 V is not enough to make Vo reversed at the critical point of 2 V. Then the hysteresis generation unit generates a hysteresis range of 1.8 V to 2.2 V. It should be understood that generation of the hysteresis range may be based on a magnitude of disturbance subjected by the reverse current switch.

Optionally, in the embodiment of the present disclosure, currents of other MOS transistors in the comparison unit may also be adjusted to generate a certain hysteresis range. For example, the second MOS transistor in FIG. 4 or FIG. 6 may be replaced by ten sub-MOS transistors, and a current of each of the sub-MOS transistors may be 1/10 of the current of the second MOS transistor in FIG. 4 or FIG. 6. Similarly, assuming that a critical point voltage Vo at which the reverse current switch is flipped is 2 V, and the reverse current switch is subjected to disturbance of 0.1 V, when Vdda is greater than Vddb at a certain time, gates of five sub-MOS transistors are connected to Vbp, and gates of the other five sub-MOS transistors are connected to GND, and Vo is close to 2 V, and the hysteresis generation unit may control gates of three sub-MOS transistors in the five sub-MOS transistors connected to the bias unit to be connected to the GND, so that Vo decreases to 1.8 V, that is, the disturbance of 0.1 V is not enough to make Vo reversed at the critical point of 2 V. Similarly, when Vdda is less than Vddb at a certain time, gates of five sub-MOS transistors are connected to Vbp, and gates of the other five sub-MOS transistors are connected to GND, and Vo is close to 2 V, and the hysteresis generation unit may control gates of three sub-MOS transistors in the five sub-MOS transistors connected to the GND to be connected to the Vbp, so that Vo increases to 2.2 V, and similarly, the disturbance of 0.1 V is not enough to make Vo reversed at the critical point of 2 V. Then the hysteresis generation unit generates a hysteresis range of 1.8 V to 2.2 V.

It should be noted that the hysteresis generation unit may also generate a certain hysteresis range by adjusting a current of another MOS transistor in the comparison unit. The embodiment of the present disclosure is not limited to the above technical solutions.

Optionally, the hysteresis generation unit may be implemented by a selector. For example, the gate of the sub MOS transistor of FIG. 12 may be connected to a one of two selector, which is controlled by the voltage Vo of the first output end.

Optionally, as shown in FIG. 11, the reverse current switch 300 further includes an offset correction unit 350.

Generally, a comparison unit composed of a first MOS transistor, a second MOS transistor, a third MOS transistor, and a fourth MOS transistor may have an offset, for example, in a case where Vdda-Vos is less than Vddb, the reverse current switch will be turned off. Vos can be regarded as an offset voltage of the comparison unit, and when the reverse current switch is turned on, a ratio of Vos to a resistance value between Vdda and Vddb is an undetected dead zone current. Vos can usually reach 100 mV. If the resistance value between Vdda and Vddb is 1 kΩ, there will be a dead zone current of 100 uA, which is unbearable for the reverse current switch. Therefore, the reverse current switch in the embodiment of the present disclosure may further include: an offset correction unit, where when the voltage of the first input end is equal to the voltage of the second input end, the offset correction unit performs offset correction on the reverse current switch.

Specifically, a reset switch may be connected in parallel with the switch resistance unit, or a reset switch may be connected in parallel with the switch resistance unit and the voltage controlled resistance unit. When the reset switch is turned on, voltages of Vdda and Vddb may be equal. In this case, physical dimensions of the third MOS transistor and the fourth MOS transistor, such as a width to length ratio, may be fine-tuned such that a current ratio of the fourth MOS transistor to the third MOS transistor is equal to a current ratio the second MOS transistor to the first MOS transistor as much as possible. Alternatively, physical dimensions of the second MOS transistor and the first MOS transistor may be fine-tuned such that a current ratio of the second MOS transistor to the first MOS transistor is equal to a current ratio of the fourth MOS transistor to the third MOS transistor as much as possible. Alternatively, physical dimensions of any of the MOS transistors in the comparison unit may be fine-tuned at the same time such that the MOS transistors meet the above requirements. By means of offset correction for the reverse current switch, a dead zone of reverse current detection can be greatly reduced.

Optionally, in the embodiment of the present disclosure, the first input end is connected to a power supply circuit, and the second input end is connected to a load circuit, where when the voltage of the first input end is greater than the voltage of the second input end, the reverse current switch is turned on, and the power supply circuit charges a storage capacitor between the load circuit and the power supply circuit; or when the voltage of the first input end is less than the voltage of the second input end, the reverse current switch is turned off, and a storage capacitor is discharged to the load circuit.

Optionally, the power supply circuit is a wire-controlled earphone, and the load circuit is a heart rate sensor.

As mentioned above, the reverse current switch is not limited to the scenario where the wire-controlled earphone is supplied with power, and can be applied to any power supply system, such as a weak power supply system.

It should be understood that "one embodiment" or "an embodiment" mentioned throughout the specification means that particular features, structures, or characteristics in connection with the embodiment are included in at least one embodiment of the present disclosure. Therefore, "in one embodiment" or "in an embodiment" appeared throughout the specification does not necessarily mean a same embodiment. Further, the particular features, structures or characteristics may be combined in any suitable manner in one or more embodiments.

Those of ordinary skill in the art may be aware that, units and circuits of the examples described in the embodiments disclosed in this description may be implemented by electronic hardware, computer software, or a combination of the two. Whether these functions are performed by hardware or software depends on specific applications and design constraint conditions of the technical solutions. A person skilled in the art may use different methods to implement the described functions for each particular application, but it should not be considered that the implementation goes beyond the scope of this application.

In several embodiments provided by the present disclosure, it should be understood that the disclosed circuits, branches, and units may be implemented by other manners. For example, the branches described above are merely exemplary, e.g., the division of the units is merely a logic function division, other division manners may exist in practical implementation, for example, a plurality of units or components may be combined or integrated to another branch, or some features may be omitted or not implemented.

If the integrated unit is implemented in the form of the software functional unit and is sold or used as an independent product, it may be stored in a computer readable storage medium. Based on such understanding, the technical solutions of the present disclosure substantially, or the part of the present disclosure making contribution to the prior art, or a part of the technical solution may be embodied in the form of a software product, and the computer software product is stored in a storage medium, which includes multiple instructions enabling computer equipment (which may be a personal computer, a server, network equipment or the like) to execute all of or part of the steps in the methods of the embodiments of the present disclosure. The foregoing storage medium includes a variety of media capable of storing program codes, such as a USB disk, a mobile hard disk, a read-only memory (ROM), a random access memory (RAM), a magnetic disk, an optical disk.

Described above are the specific embodiments of the present disclosure only, but the protection scope of present disclosure is not limited thereto, those skilled who are familiar with the art could readily think of variations or substitutions within the technical scope disclosed by the present disclosure, and these variations or substitutions shall fall within the protection scope of the present disclosure. Therefore, the protection scope of the present disclosure should be determined with reference to the protection scope of the claims.

What is claimed is:

1. A reverse current switch, comprising:
   a comparison unit comprising a first input end, a second input end, and a first output end; and
   a switch resistance unit, wherein a first end of the switch resistance unit is connected to the first input end, a second end of the switch resistance unit is connected to the second input end, and a third end of the switch resistance unit is connected to the first output end,
   wherein the switch resistance unit is controlled by a voltage of the first output end;
   when a voltage of the first input end is greater than a voltage of the second input end, the voltage of the first output end controls the switch resistance unit to be in an on state; or
   when a voltage of the first input end is less than a voltage of the second input end, the voltage of the first output end controls the switch resistance unit to be in an off state;
   wherein the reverse current switch further comprises:
   a voltage controlled unit comprising a voltage controlled resistance unit and a voltage controlled voltage generation unit, wherein the voltage controlled resistance unit and the switch resistance unit are connected in series between the first input end and the second input end, the voltage controlled voltage generation unit is connected in parallel with the comparison unit, and voltage controlled voltage generation unit comprises a second output end, wherein when a difference between the voltage of the first input end and the voltage of the second input end increases, a voltage of the second output end controls a resistance value of the voltage controlled resistance unit to decrease.

2. The reverse current switch according to claim 1, wherein when the difference between the voltage of the first input end and the voltage of the second input end decreases, the voltage of the second output end controls the resistance value of the voltage controlled resistance unit to increase.

3. The reverse current switch according to claim 1, wherein the comparison unit comprises:
a first metal-oxide-semiconductor (MOS) transistor, a second MOS transistor, a third MOS transistor, and a fourth MOS transistor, wherein a gate of the first MOS transistor is connected to a gate of the second MOS transistor, a gate of the third MOS transistor is connected to a gate of the fourth MOS transistor and a source of the third MOS transistor is connected to a source of the fourth MOS transistor, a drain of the first MOS transistor is connected to a drain of the third MOS transistor, a drain of the second MOS transistor and a drain of the fourth MOS transistor are respectively connected to the first output end, a source of the first MOS transistor is connected to the first input end, and a source of the second MOS transistor is connected to the second input end.

4. The reverse current switch according to claim 3, wherein the first MOS transistor and the second MOS transistor are PMOS transistors, the third MOS transistor and the fourth MOS transistor are NMOS transistors, the gate of the third MOS transistor and the gate of the fourth MOS transistor are respectively connected to a bias unit, and the source of the first MOS transistor is connected to the drain of the first MOS transistor.

5. The reverse current switch according to claim 4, wherein the voltage controlled resistance unit and the switch resistance unit are connected in series between the first input end and the source of the second MOS transistor; the voltage controlled voltage generation unit comprises a fifth MOS transistor that is a PMOS transistor and a first resistor, a drain of the fifth MOS transistor and one end of the first resistor are respectively connected to the second output end, a source of the fifth MOS transistor is connected to the second input end, a gate of the fifth MOS transistor is connected to the gate of the first MOS transistor, and the other end of the first resistor is connected to the source of the third MOS transistor; and the voltage controlled resistance unit is controlled by the voltage of the second output end.

6. The reverse current switch according to claim 3, wherein the first MOS transistor and the second MOS transistor are PMOS transistors, the third MOS transistor and the fourth MOS transistor are NMOS transistors, the gate of the first MOS transistor and the gate of the second MOS transistor are respectively connected to a bias unit, and the source of the third MOS transistor is connected to the drain of the third MOS transistor.

7. The reverse current switch according to claim 6, wherein the voltage controlled resistance unit and the switch resistance unit are connected in series between the first input end and the source of the second MOS transistor; the voltage controlled voltage generation unit comprises a fifth MOS transistor that is an NMOS transistor and a first resistor, a drain of the fifth MOS transistor and one end of the first resistor are respectively connected to the second output end, the other end of the first resistor is connected to the second input end, a gate of the fifth MOS transistor is connected to the gate of the third MOS transistor, and a source of the fifth MOS transistor is connected to the source of the third MOS transistor; and the voltage controlled resistance unit is controlled by the voltage of the second output end.

8. The reverse current switch according to claim 3, further comprising:
a hysteresis generation unit,
wherein when the voltage of the first input end is greater than the voltage of the second input end, the hysteresis generation unit increases a current of the fourth MOS transistor and/or decreases a current of the second MOS transistor; or
when the voltage of the first input end is less than the voltage of the second input end, the hysteresis generation unit decreases a current of the fourth MOS transistor and/or increases a current of the second MOS transistor.

9. The reverse current switch according to claim 1, further comprising:
an offset correction unit,
wherein when the voltage of the first input end is equal to the voltage of the second input end, the offset correction unit performs offset correction on the reverse current switch.

10. The reverse current switch according to claim 1, wherein the switch resistance unit comprises a sixth MOS transistor and a second resistor in series, and a gate of the sixth MOS transistor is controlled by the voltage of the first output end.

11. The reverse current switch according to claim 1, wherein the voltage controlled resistance unit comprises a seventh MOS transistor and a third resistor in parallel, and a gate of the seventh MOS transistor is controlled by the voltage of the second output end.

12. The reverse current switch according to claim 1, wherein the first input end is connected to a power supply circuit, and the second input end is connected to a load circuit,
wherein when the voltage of the first input end is greater than the voltage of the second input end, the power supply circuit charges a storage capacitor between the load circuit and the power supply circuit.

13. The reverse current switch according to claim 12, wherein the power supply circuit is a wire-controlled earphone, and the load circuit is a heart rate sensor.

14. The reverse current switch according to claim 1, wherein the first input end is connected to a power supply circuit, and the second input end is connected to a load circuit,
when the voltage of the first input end is less than the voltage of the second input end, a storage capacitor is discharged to the load circuit.

15. The reverse current switch according to claim 14, wherein the power supply circuit is a wire-controlled earphone, and the load circuit is a heart rate sensor.

16. A reverse current switch, comprising:
a comparison unit comprising a first input end, a second input end, and a first output end; and
a switch resistance unit, wherein a first end of the switch resistance unit is connected to the first input end, a second end of the switch resistance unit is connected to the second input end, and a third end of the switch resistance unit is connected to the first output end,
wherein the switch resistance unit is controlled by a voltage of the first output end;
when a voltage of the first input end is greater than a voltage of the second input end, the voltage of the first output end controls the switch resistance unit to be in an on state; or
when a voltage of the first input end is less than a voltage of the second input end, the voltage of the first output end controls the switch resistance unit to be in an off state;
wherein the reverse current switch further comprises:
a voltage controlled unit comprising a voltage controlled resistance unit and a voltage controlled voltage generation unit, wherein the voltage controlled resistance unit and the switch resistance unit are connected in series between the first input end and the second input end, the voltage controlled voltage generation unit is connected in parallel with the comparison unit, and voltage controlled voltage generation unit comprises a second output end,
when a difference between the voltage of the first input end and the voltage of the second input end decreases, a voltage of the second output end controls a resistance value of the voltage controlled resistance unit to increase.

17. A reverse current switch, comprising:
a comparison unit comprising a first input end, a second input end, and a first output end; and
a switch resistance unit, wherein a first end of the switch resistance unit is connected to the first input end, a second end of the switch resistance unit is connected to the second input end, and a third end of the switch resistance unit is connected to the first output end,
wherein the switch resistance unit is controlled by a voltage of the first output end:
when a voltage of the first input end is greater than a voltage of the second input end, the voltage of the first output end controls the switch resistance unit to be in an on state; or
when a voltage of the first input end is less than a voltage of the second input end, the voltage of the first output end controls the switch resistance unit to be in an off state;
wherein the comparison unit comprises:
a first metal-oxide-semiconductor (MOS) transistor, a second MOS transistor, a third MOS transistor, and a fourth MOS transistor, wherein a gate of the first MOS transistor is connected to a gate of the second MOS transistor, a gate of the third MOS transistor is connected to a gate of the fourth MOS transistor and a source of the third MOS transistor is connected to a source of the fourth MOS transistor, a drain of the first MOS transistor is connected to a drain of the third MOS transistor, a drain of the second MOS transistor and a drain of the fourth MOS transistor are respectively connected to the first output end, a source of the first MOS transistor is connected to the first input end, and a source of the second MOS transistor is connected to the second input end.

* * * * *